United States Patent [19]

Asahina et al.

[11] Patent Number: 4,943,987
[45] Date of Patent: Jul. 24, 1990

[54] METHOD AND SYSTEM FOR DISPLAYING X-RAY IMAGES OF BLOOD-VESSEL STRUCTURE PARTS OF SUBJECT

[75] Inventors: Hiroshi Asahina, Tochigi; Ichiro Ogura, Ootawara, both of Japan

[73] Assignee: Kabushiki Kaisha Toshiba, Kawasaki, Japan

[21] Appl. No.: 430,964

[22] Filed: Nov. 1, 1989

Related U.S. Application Data

[63] Continuation of Ser. No. 228,157, Aug. 4, 1988, abandoned.

[30] Foreign Application Priority Data

Aug. 7, 1987 [JP] Japan ................................ 62-198422
Aug. 7, 1987 [JP] Japan ................................ 62-198423

[51] Int. Cl.$^5$ ............................................... H04N 5/32
[52] U.S. Cl. ......................................... 378/99; 378/62; 358/111
[58] Field of Search ................... 378/99, 901, 95, 62; 358/111; 364/413.23, 413.18

[56] References Cited

U.S. PATENT DOCUMENTS

| | | | |
|---|---|---|---|
| 4,433,428 | 2/1984 | Haendle et al. ................ | 378/99 |
| 4,542,459 | 9/1985 | Riederer . | |
| 4,559,557 | 12/1985 | Keyes et al. ................... | 364/413.23 |
| 4,692,864 | 9/1987 | Shimoni et al. ................ | 378/99 |
| 4,706,268 | 11/1987 | Onodera ......................... | 378/99 |
| 4,709,385 | 11/1987 | Pfeiler et al. ................... | 378/99 |

FOREIGN PATENT DOCUMENTS 3026897 2/1981 Fed. Rep. of Germany .
3124583 12/1982 Fed. Rep. of Germany .
3738636 6/1988 Fed. Rep. of Germany .

OTHER PUBLICATIONS

W. Seyferth et al., "Pfadfindertechnik: eine Erganzung der Digitalen Subtraktionsangiographie im fluoroskopischen Betrieb," Electromedica, 53, (1985), pp. 39–45.

Primary Examiner—Carolyn E. Fields
Assistant Examiner—David P. Porta
Attorney, Agent, or Firm—Finnegan, Henderson, Farabow, Garrett, and Dunner

[57] ABSTRACT

X-ray mask images of a subject are acquired by a TV camera before a contrast media injected by a injector reaches a region of interest of the subject, the acquired X-ray mask images are stored in a mask image memory in accordance with a frame counter and a memory controller. X-ray contrast images of the subject are acquired by the TV camera after the contrast media reaches the region of interest of the subject, the acquired X-ray contrast images are stored in a contrast image memory in accordance with a frame counter and a memory controller. The mask images and contrast images are subtracted by a subtraction processor, and X-ray subtraction images are obtained. The X-ray images of the subject acquired by the TV camera and the X-ray subtraction images are superimposed by a superimposition processor, and then are displayed on a TV monitor.

9 Claims, 8 Drawing Sheets

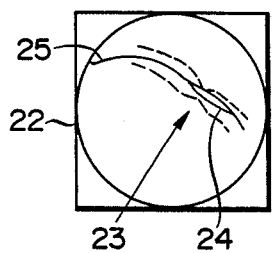 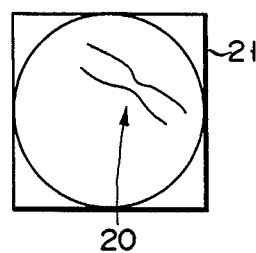
FIG. 1A    FIG. 1B
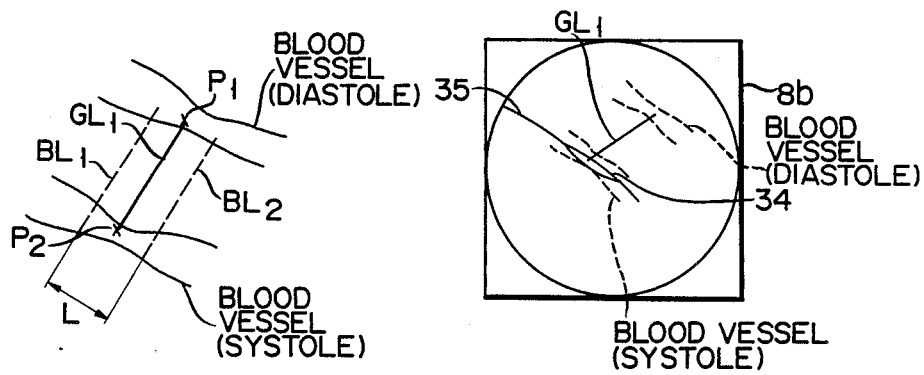
FIG. 3A    FIG. 3B
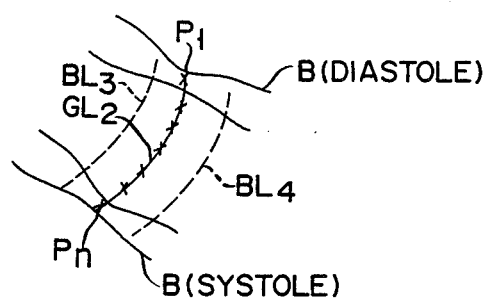
FIG. 6

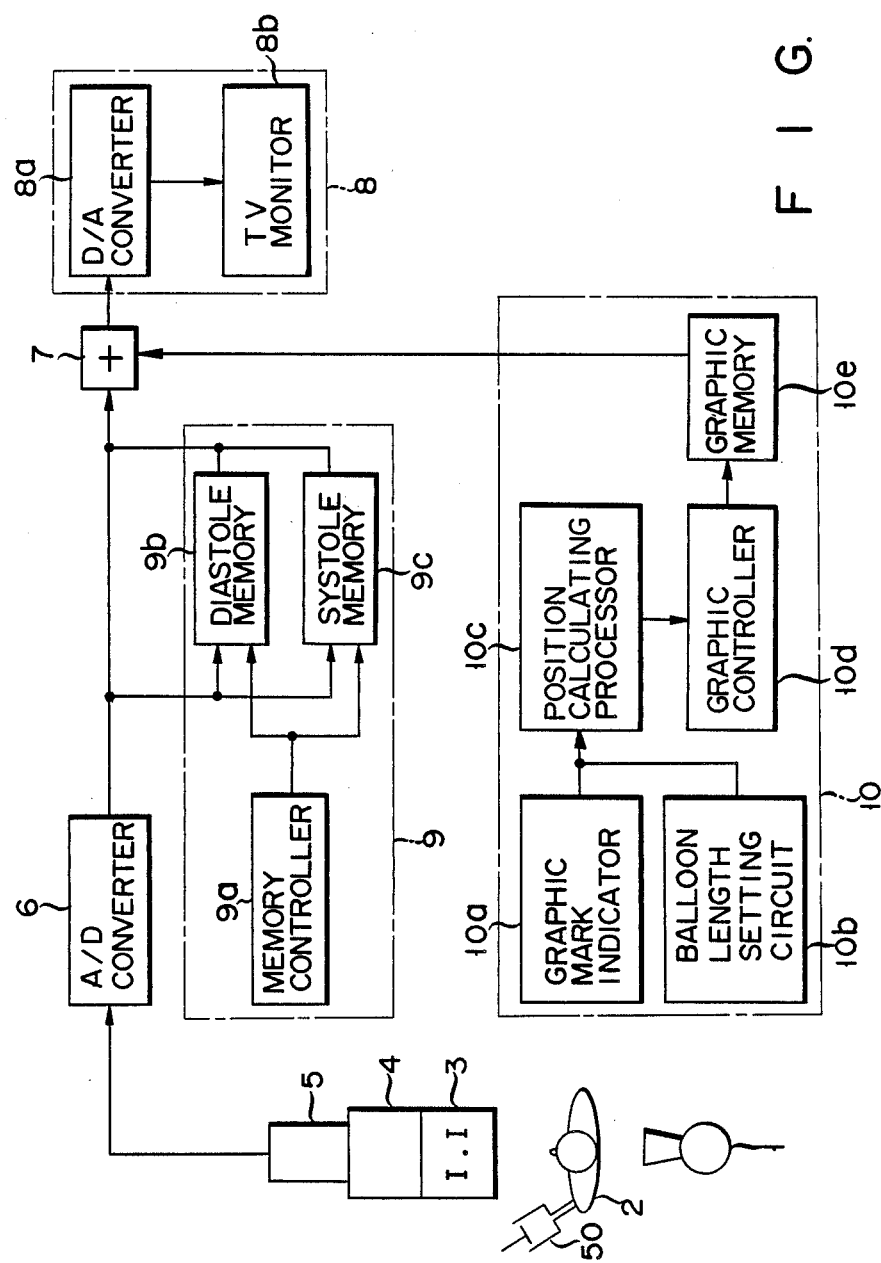

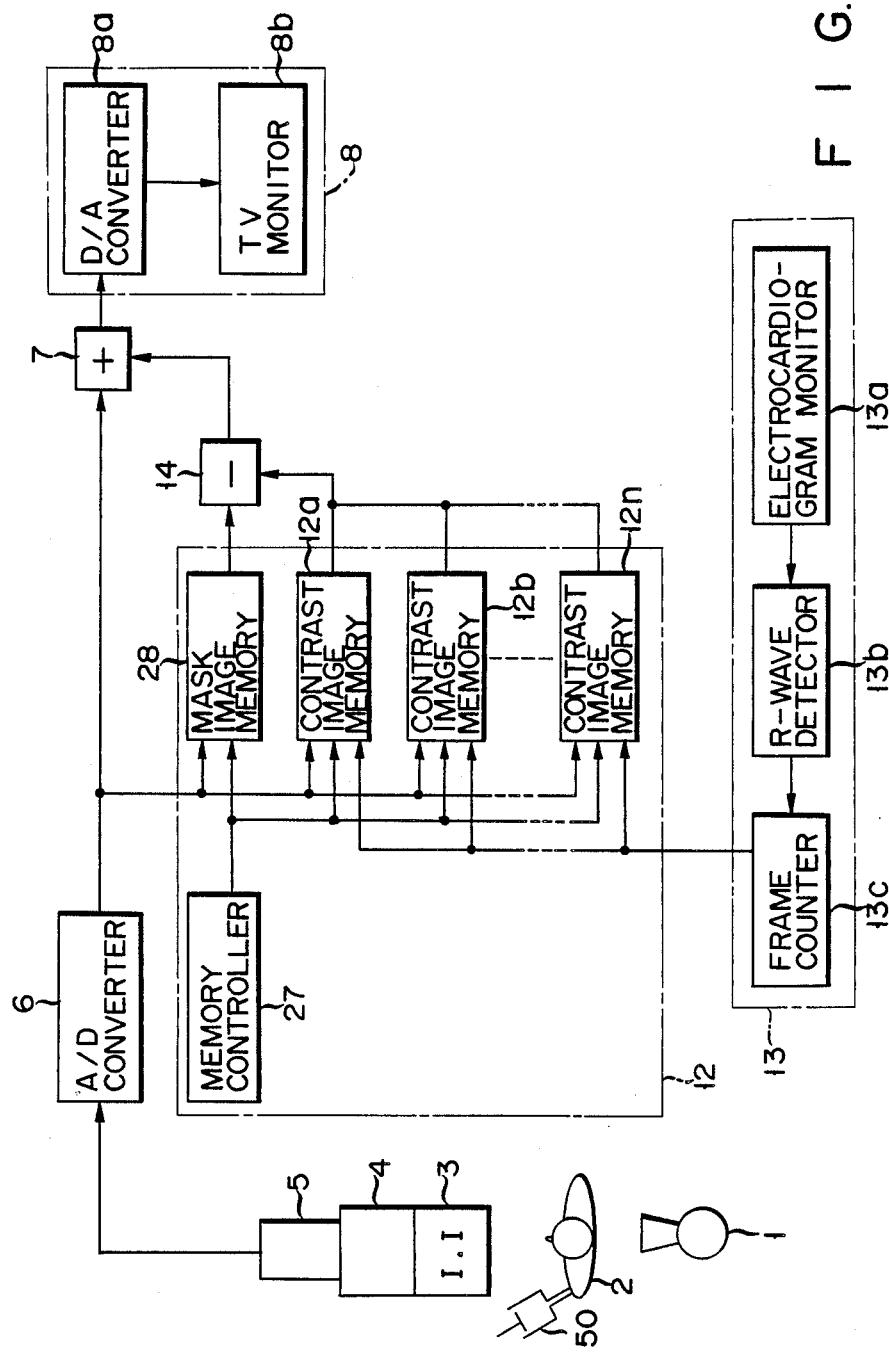

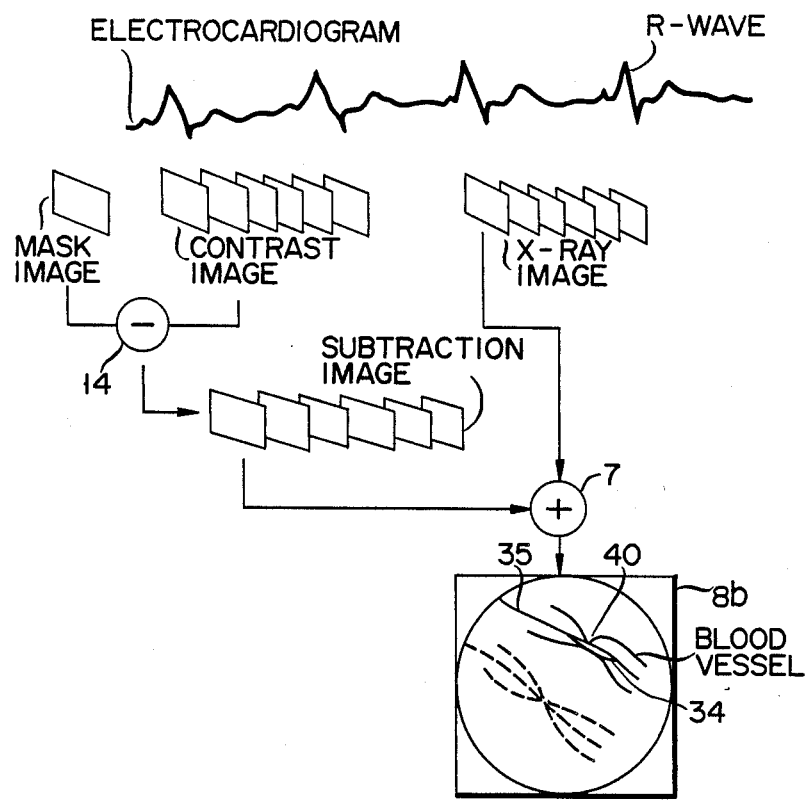
F I G. 8

METHOD AND SYSTEM FOR DISPLAYING X-RAY IMAGES OF BLOOD-VESSEL STRUCTURE PARTS OF SUBJECT

This application is a continuation of application Ser. No. 07/228,157, filed Aug. 4, 1988, now abandoned.

BACKGROUND OF THE INVENTION

1. Field of the Invention

The present invention relates to a method and system for displaying X-ray images in blood-vessel stricture parts of a subject.

2. Description of the Related Art

Conventionally, a recovery operation for a blood-vessel stricture part of a subject is performed by inserting a catheter toward the blood-vessel stricture part, locating a balloon attached to the catheter at the stricture part and then expanding the balloon. By this operation the blood-vessel stricture part can be restored to the previous diameter.

The above-mentioned operation is performed while an X-ray image of the blood-vessel stricture part of the subject is displayed on a television monitor and the displayed image is observed by a doctor. Otherwise a new type of apparatus is used for catheter operation which has been developed because of advances in image processing techniques resulting from the recent spread of integrated-circuit (IC) memories. According to this apparatus, as shown in FIGS. 1A and 1B, contrast image 20, which well reproduces a blood-vessel stricture part, is previously stored in an IC memory, the contrast image is then converted into analog information to be displayed on television monitor 21, and a doctor operates a catheter while comparing the contrast image with X-ray image 23 displayed on X-ray monitor 22.

With such apparatus, however, by the comparison between contrast image 20 of blood-vessel stricture part displayed on TV monitor 21 and X-ray image 23 of catheter 25 with balloon 24 displayed on X-ray monitor 22, the doctor will only assume the true position of blood-vessel stricture part on X-ray image 23. Thus, it is difficult to know the accurate positional relation between blood-vessel stricture part and catheter 25 having balloon 24, and the operation of catheter 25 is not easy.

Moreover, although contrast image 20 of blood-vessel stricture part is displayed as a still image on TV monitor 21, since the blood vessel moves actually in accordance with the heart beats of the subject the still-image display alone will not permit sufficient operations of catheter 25.

Thus, the apparatus is desired which can definitely display a positional relation between a blood-vessel stricture part and a catheter with a balloon.

Summary of the Invention

It is an object of the present invention to provide a method and system for displaying an X-ray image of a blood-vessel stricture part of a subject under examination.

According to one aspect of the present invention, there is provided a system for displaying X-ray images in a region of interest of a subject, the system comprising injection means for injecting a contrast media into the subject, image acquiring means for acquiring X-ray images in the region of interest of the subject, image storing means for storing X-ray images acquired by the image acquiring means after the contrast media injected by the injection means reaches the region of interest of the subject, graphic data generating means for generating graphic data by using the X-ray images stored in the image storing means, superimposition means for superimposing the graphic data generated by the graphic data generating means on X-ray images acquired by the image acquiring means, thereby obtaining X-ray superimposition images, and display means for displaying the X-ray superimposition images obtained by the superimposition means.

According to another aspect of the present invention, there is provided a system for displaying X-ray images in a region of interest of a subject, the system comprising injection means for injecting a contrast media into the subject, image acquiring means for acquiring X-ray images in the region of interest of the subject, first image storing means for storing at least first one of X-ray images acquired by the image acquiring means before the contrast media injected by the injection means reaches the region of interest of the subject, second image storing means for storing second X-ray images acquired by the image acquiring means after the contrast media injected by the injection means reaches the region of interest of the subject, selection means for selecting the first and second image storing means, subtraction means for subtracting the second X-ray images stored in the second image storing means from at least the first one of X-ray images stored in the first image storing means, thereby obtaining X-ray subtraction images, superimposition means for superimposing the X-ray subtraction images obtained by the subtraction means on third X-ray images acquired by the image acquiring means, thereby obtaining X-ray superimposition images, and display means for displaying X-ray superimposition images obtained by the superimposition means.

Brief Description of the Drawings

FIGS. 1A and 1B show display examples of an X-ray image and a contrast image in a conventional apparatus;

FIG. 2 is a block diagram of a first embodiment of the present invention;

FIGS. 3A and 3B show display examples of an X-ray image and a graphic line in the first embodiment;

FIG. 6 shows a display example of an X-ray image and a graphic line in the second embodiment;

FIG. 7 is a block diagram of a third embodiment of the present invention;

FIG. 8 shows an operational procedure of the third embodiment;

Detailed Description of the Preferred Embodiments

Figure 4A:
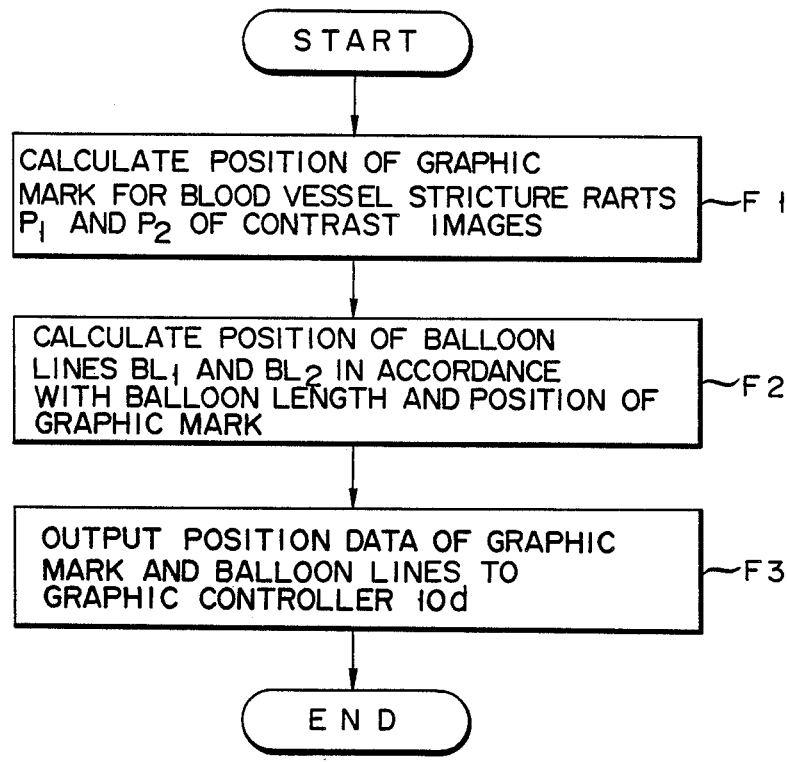
FIGS. 4A and 4B are operational flowcharts of the position calculating processor and the graphic controller in the first embodiment.

Referring now to FIG. 2, X rays generated by X-ray tube 1 are transmitted through subject 2 under examination, and converted by image intensifier (I, I) 3 to light rays which are directed to optical system 4. An X-ray image of subject 2 is formed by the light rays incident on optical system 4. The X-ray image thus formed is taken by TV camera 5 and converted into a digital signal by analog/digital (A/D) converter 6. It is to be noted here that an X-ray image is obtained by irradiation of a blood vessel of subject 2, moving in synchronism with the heartbeats, with X rays generated by X-ray tube 1, and a contrast image is obtained by radiation of the X rays for the blood vessel while a contrast medium is injected into the blood vessel by injector 50.

The contrast image taken by TV camera 5 is stored in storage device 9 via A/D converter 6. Position data representing a locus of positions of the blood vessel resulting from the heartbeats of subject 2 is generated by position data generator 10 on the basis of the contrast image stored in storage device 9. The position data generated by position data generator 10 is superimposed upon the X-ray image taken by TV camera 5 in superimposer 7, and the superimposed image is displayed by display device 8.

Storage device 9 comprises diastole memory 9b, systole memory 9c, and memory controller 9a for controlling the timing of access to diastole and systole memories 9b and 9c. More specifically, a contrast image of the blood vessel in a diastole of the heart of subject 2 is stored in diastole memory 9b, and a contrast image in a systole of the heart is stored in systole memory 9c.

Position data generator 10 comprises graphic mark indicator 10a, balloon-length setting circuit 10b, position calculating processor 10c, graphic controller 10d, and graphic memory 10e. More specifically, graphic mark indicator 10a specifies graphic marks on positions of blood-vessel stricture parts P1 and P2 in contrast images in the diastole and systole of the heart of the subject which are displayed on TV monitor 8b. Balloon-length setting circuit 10b sets the length L of balloon 34 attached to catheter 35 to be inserted toward the blood-vessel stricture part of subject 2. Position calculating processor 10c calculates the positions of blood-vessel stricture parts P1 and P2 specified by graphic mark indicator 10a. Graphic controller 10d generates graphic data for displaying a graphic line GL1 connecting blood-vessel stricture parts P1 and P2 in accordance with the results of calculations by position calculating processor 10c. Graphic memory 10e stores the graphic line data generated by graphic controller 10d. Position calculating processor 10c also generates data on positions of balloon lines BL1 and BL2 which are in parallel with graphic line GL1 and spaced by the balloon length L set by the balloon-length setting circuit 10b.

Graphic controller 10d generates graphic data for displaying balloon lines BL1 and BL2 in accordance with the data indicating the positions of BL1 and BL2 generated by position calculating processor 10c. Graphic memory 10e stores the graphic data for BL1 and BL2.

Display device 8 comprises D/A converter 8a for converting output data of adder 7 to an analog signal, and TV monitor 8b for visually displaying the analog signal output from D/A converter 8a.

In operation, after a contrast medium is injected into the blood-vessel stricture part, a contrast image obtained by TV camera 5 is stored in storage device 9 via A/D converter 6. In this case, in the diastole of the heart of subject 2, the contrast image is stored in diastole memory 9b by memory controller 9a. Similarly, in the systole of the heart, the contrast image is stored in systole memory 9c by memory controller 9a.

Graphic mark indicator 10a outputs a graphic mark indicating signal to position calculating processor 10c. Position calculating processor 10c outputs position data indicating the center of the screen of TV monitor 8b to graphic controller 10d in accordance with the graphic mark indicating signal. Graphic controller 10d generates graphic mark data used for drawing a graphic mark on the center position of the screen of TV monitor 8b and writes the graphic mark data into that memory location of graphic memory 10e which corresponds to the center of the screen of TV monitor 8b.

Superimposer 7 superimposes the graphic mark data stored in graphic memory 10e and the contrast image stored in diastole memory 9a and then provides the graphic-mark-superimposed image to D/A converter 8a. D/A converter 8a converts the graphic-mark-superimposed image to analog data and then provides the analog data to TV monitor 8b.

According to the above processes, the contrast image obtained in the diastole of the heart and the graphic mark are simultaneously displayed on TV monitor 8b. At this time, graphic mark indicator 10a commands for the graphic mark to be located at the blood-vessel stricture part P1.

In addition, the graphic mark data is also superimposed on the contrast image stored in systole memory 9b, and the graphic-mark-superimposed image is displayed on TV monitor 8b. Graphic mark indicator 10a commands so as to locate the graphic mark at the position P2 corresponding to the blood-vessel stricture part in the systole of the heart.

Figure 4B:
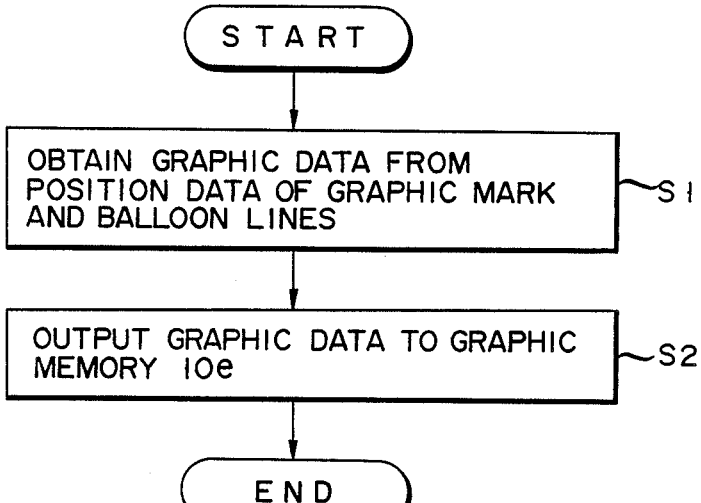

The operations of position calculating processor 10c and graphic controller 10d will be described with reference to FIGS. 4A and 4B.

In step F1, position calculating processor 10c is commanded by graphic mark indicator 10a to calculate the positions of graphic marks for blood-vessel stricture parts P1 and P2 in the contrast images in the diastole and systole of the heart. In step F2, the positions of balloon lines BL1 and BL2 parallel with graphic line GL1 connecting blood-vessel stricture parts P1 and P2 are calculated on the basis of graphic line GL1 and the balloon length L set by balloon length setting circuit 10b. The calculated position data of BL1 and BL2 is output to graphic controller 10d in step F3.

Subsequently, in step S1, graphic controller 10d obtains graphic data for balloon lines BL1 and BL2 from the position data of BL1 and BL2 provided from position calculating processor 10c, and, in step S2, the obtained graphic data is stored in graphic memory 10e. The graphic data is provided to TV monitor 8b via graphic memory 10e, adder 7 and D/A converter 8a.

Thus, balloon lines BL1 and BL2 are drawn to be parallel with graphic line GL1 and at a distance of ½L from graphic line GL1 on the opposite sides thereof. The graphic data of graphic line GL1 and balloon lines BL1 and BL2 are stored in graphic memory 10e.

After the above processes, the image data displayed on TV monitor 8b is cleared. Subsequently an X-ray image taken by TV camera 5 and graphic data stored in graphic memory 10e are superimposed in superimposer 7 and then converted by D/A converter 8a to analog data for outputting TV monitor 8b.

As described above and as shown in FIG. 3A, on the screen of TV monitor 8b is graphic line GL1 indicating a locus of the movement of the blood-vessel stricture part from a diastole till a systole of the heart of subject 2. This permits a definite positional relation between the blood-vessel stricture part and catheter 35 with balloon 34 used in a recovery operation for the stricture part of the blood vessel, and easy operation of catheter 35.

Further, in this case, since balloon lines BL1 and BL2 are displayed on both sides of graphic line GL1, the location of balloon 34 at the blood vessel stricture part is made easier.

Next, the system of a second embodiment will be described.

Figure 5:
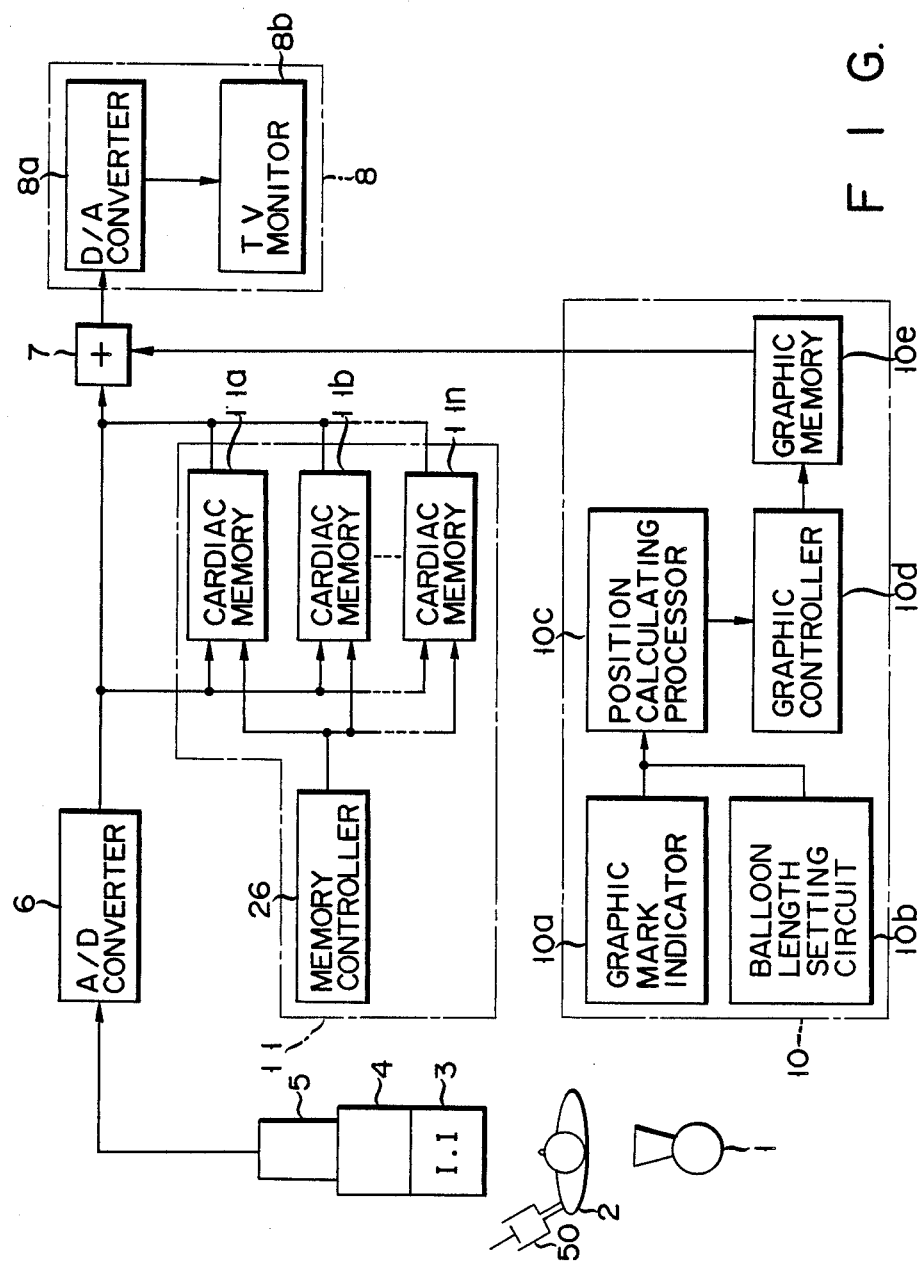
FIG. 5 is a block diagram of a second embodiment of the present invention.

The second embodiment shown in FIG. 5 differs from the first embodiment in the arrangement of the storage device. That is, in the second embodiment, storage device 11 has a plurality of cardiac memories 11a, 11b, ... 11n for storing a plurality of contrast images to be obtained during a period from a diastole till a systole of the heart of subject 2.

In the system, by injecting a contrast medium into a blood vessel, contrast images obtained during a period from a diastole till a systole of the heart of subject 2 are stored in cardiac memories 11a, 11b, ... 11n by memory controller 26. A contrast image of the blood vessel in the diastole of the heart is read out from memory 11a to be displayed on TV monitor 8b, and the same operations as those in the first embodiment are performed so as to locate graphic mark P1 on the blood-vessel stricture part as shown in FIG. 6. The operation is also performed for each of contrast images stored in memories 11b, ... 11n. As a result, graphic marks P1, ... Pn indicating a locus of the movement of the blood-vessel stricture part from a diastole till a systole of the heart are drawn on the screen of TV monitor 8b.

Graphic marks P1, ... Pn are connected by graphic line GL2. Furthermore, balloon lines BL3 and BL4 are drawn on both sides of graphic line GL2. Graphic data for graphic line GL2 and balloon lines BL3 and BL4 is stored in graphic memory 10e. By the superimposed display of graphic data and an X-ray mask image on TV monitor 8b, catheter 35 having balloon 34 is made easy to operate. That is, since graphic line GL2 displayed on TV monitor 8b indicates the locus of the actual movement of the blood-vessel stricture part, the accurate location of balloon 34 at the blood-vessel stricture part can be effected by operation of catheter 35.

A third embodiment of the present invention will be described with reference to FIGS. 7 and 8. The system of the third embodiment agrees with the first embodiment except storage device 12, memory select signal generator 13, subtraction device 14 and superimposer 7. That is, storage device 12 stores, as a mask image, an X-ray image obtained by photographing subject 2 exposed to X-ray radiation before the contrast medium injected into subject 2 reaches the blood-vessel stricture part thereof, and stores, as a contrast image, an X-ray image of subject 2 photographed after the contrast medium reaches the blood-vessel stricture part. Memory select signal generator 13 generates memory select signals used for selecting one of memories (to be described later) in storage device 12, which store contrast images, on the basis of an electrocardiogram obtained from subject 2. Subtraction device 14 performs subtraction between a mask image and a contrast image to form an image of blood vessels alone, viz. a subtraction image. Superimposer 7 superimposes a subtraction image obtained by subtraction device 14 upon an X-ray image obtained by TV camera 5.

Storage device 12 comprises mask image memory 28 for storing a mask image, a plurality of contrast image memories 12a, 12b, ... 12n for storing contrast images, and memory controller 27 for controlling the timing of access to these memories. The memories are all coupled to A/D converter 6.

Memory select signal generator 13 comprises electrocardiogram monitor 13a for monitoring an electrocardiogram obtained from subject 2, R-wave detector 13b for detecting an R-wave in the electrocardiogram waveform monitored by monitor 13a, and frame counter 13c, which is initialized by the R-wave detected by detector 13b, for generating and applying count signals at the frame display rate of display device 8 to contrast image memories 12a, 12b, ... 12n, as memory select signals.

The mask image is written into mask image memory 28 by a write signal provided from memory controller 27. The contrast images obtained by TV camera 5 after the detection of the R-wave in the electrocardiogram are in sequence stored in contrast image memories 12a, 12b, ... 12n in accordance with the write signal provided by memory controller 27 and the memory select signals provided from frame counter 13c. In addition, the contrast images stored in contrast image memories 12a, 12b, ... 12n are input subtraction device 14 by the memory select signals.

Subtraction device 14 subtracts the mask image always provided by mask image memory 28 from each of the contrast images sequentially read out from contrast image memories 12a, 12b, ... 12n and provides the subtraction results to superimposer 7 as the subtraction images.

Superimposer 7 superimposes a subtraction image obtained by subtraction device 14 on an X-ray image obtained by TV camera 5, in the same phase of both images, and provides the superimposed images to display device 8. As a result, as shown in FIG. 8, a contrast image of blood-vessel stricture part 40 and an X-ray image of catheter 35 with balloon 34, which are of the same heartbeat-phase, are displayed on the screen of TV monitor 8a. Therefore, it will be understood that the positioning of catheter 35 becomes easy during a recovery operation for the blood-vessel stricture part.

Figure 9:
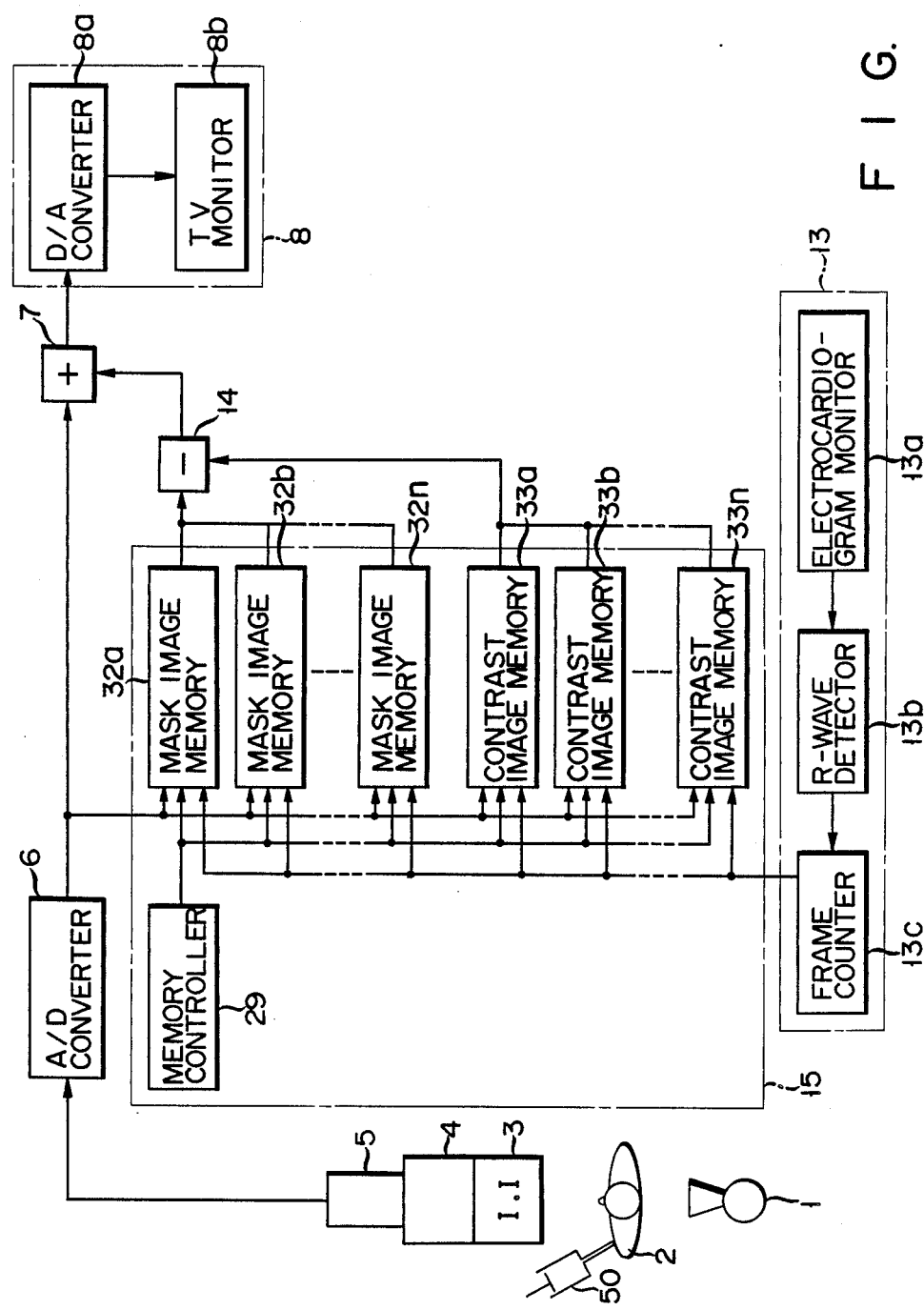
FIG. 9 is a block diagram of a fourth embodiment of the present invention.

FIG. 9 is a block diagram of a fourth embodiment which includes, unlike the third embodiment, a plurality of mask image memories 32a, 32b, ... 32n. In this embodiment, the mask image memories are responsive to memory select signals from frame counter 13c to sequentially store a mask image of one frame. For example, a mask image of a frame immediately following the detection of R-wave is stored in memory 32a, and a mask image of the next frame is stored in memory 32b. In addition, mask and contrast images which are of the same heartbeat-phase, are read out from the mask image and contrast image memories by the memory select signals, and the subtraction between the corresponding images is sequentially performed. As a result, subtraction images can be obtained without artifacts due to the heartbeats.

Figure 10:
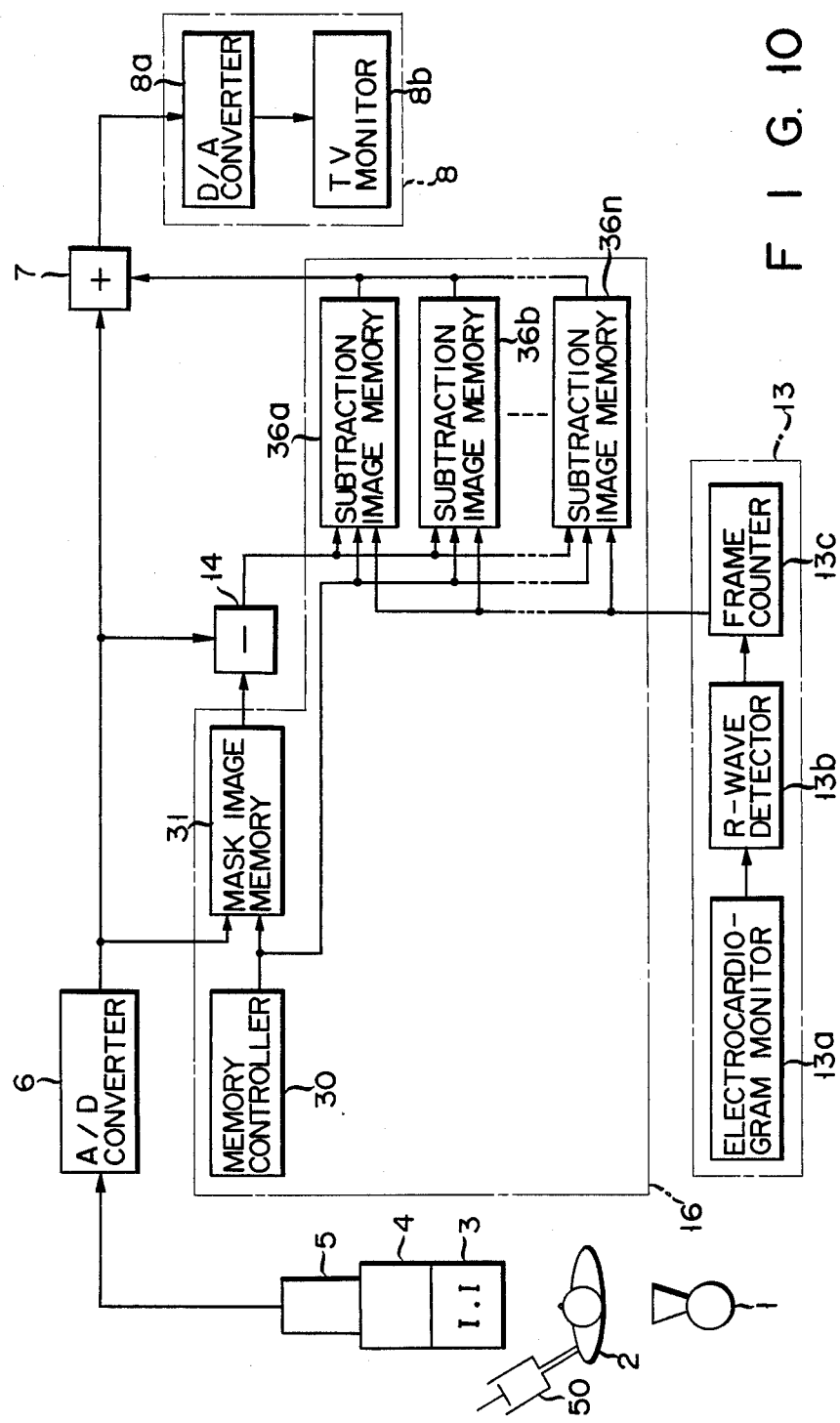
FIG. 10 is a block diagram of a fifth embodiment of the present invention.

FIG. 10 shows an arrangement of a fifth embodiment which is provided with a plurality of subtraction image memories 36a, 36b, ... 36n in place of the contrast image memories used in the third embodiment. The fifth embodiment can also provide the same effects as the third embodiment. Further, in this embodiment, using a plurality of mask image memories, it would be provided the same effects as those of the fourth embodiment.

Although the preferred embodiments of the present invention have been described and disclosed, it is apparent that other embodiments and modifications are possible.

What is claimed is:

1. A method for generating and displaying X-ray images of a region of interest of a subject, the method comprising the steps of:
   injecting a contrast media into the subject;
   acquiring X-ray contrast images of the region of interest of the subject after the contrast media reaches the region of interest of the subject;
   generating graphic line data representing a locus of changing position of the region of interest by using the X-ray contrast images;
   acquiring X-ray images in the region of interest of the subject;
   superimposing the graphic line data on X-ray images to obtain X-ray superimposition images; and
   displaying the X-ray superimposition images.

2. A method according to claim 1, wherein the graphic line data includes data for indicating a balloon length and data for indicating the region of interest of the subject.

3. A method for generating and displaying X-ray images of a region of interest of a subject, the method comprising the steps of:
   injecting a contrast media into the subject;
   acquiring at least one X-ray mask image of the region of interest of the subject before the contrast media reaches the region of interest of the subject;
   acquiring X-ray contrast images of the region of interest of the subject after the contrast media reaches the region of interest of the subject;
   subtracting the X-ray contrast images from the at least one X-ray mask image to obtain X-ray subtraction images;
   acquiring X-ray images of the region of interest of the subject;
   superimposing the X-ray subtraction images on the X-ray images to obtain X-ray superimposition images; and
   displaying X-ray superimposition images.

4. A system for generating and displaying X-ray images of a region of interest of a subject, the system comprising:
   injection means for injecting a contrast media into the subject;
   image acquiring means for acquiring X-ray images of the region of interest of the subject;
   image storing means for storing the X-ray images acquired by the image acquiring means after the contrast media injected by the injection means reaches the region of interest of the subject;
   graphic line data generating means for generating graphic line data representing a locus of changing position of the region of interest by using the X-ray images stored in the image storing means;
   superimposition means for superimposing the graphic line data generated by the graphic line data generating means on the X-ray images acquired by the image acquiring means to obtain X-ray superimposition images; and
   display means for displaying the X-ray superimposition images obtained by the superimposition means.

5. A system according to claim 4, wherein the graphic line data includes data for indicating a balloon length and data for indicating the region of interest of the subject.

6. A system for generating and displaying X-ray images of a region of interest of a subject, the system comprising:
   injection means for injecting a contrast media into the subject;
   image acquiring means for acquiring X-ray images of the region of interest of the subject;
   first image storing means for storing a first portion of the X-ray images acquired by the image acquiring means before the contrast media injected by the injection means reaches the region of interest of the subject;
   second image storing means for storing a second portion of the X-ray images acquired by the image acquiring means after the contrast media injected by the injection means reaches the region of interest of the subject;
   detecting means for generating a memory detection signal upon detecting a selected state of the subject;
   selection means for selecting the first and second image storing means in accordance with the memory detection signal;
   subtraction means for subtracting the second portion of the X-ray images stored in the second image storing means from the first portion of the X-ray images stored in the first image storing means to obtain X-ray subtraction images;
   superimposition means for superimposing the X-ray subtraction images obtained by the subtraction means on a third portion of the X-ray images acquired by the image acquiring means to obtain X-ray superimposition images; and
   display means for displaying the X-ray superimposition images obtained by the superimposition means.

7. A system according to claim 6, wherein the detecting means includes:
   monitoring means for monitoring electrocardiogram signals of the subject;
   R-wave detecting means for detecting R-waves of the electrocardiogram signals monitored by the monitoring means; and
   means for generating the memory selection signal in accordance with the R-waves detected by the R-wave detecting means.

8. A system for generating and displaying X-ray images of a region of interest of a subject, the system comprising:
   injection means for injecting a contrast media into the subject;
   image acquiring means for acquiring X-ray images of the region of interest of the subject;
   first image storing means for storing a first portion of the X-ray images acquired by the image acquiring means before the contrast media injected by the injection means reaches the region of interest of the subject;
   subtraction means for subtracting the first portion of the X-ray images stored in the first image storing means from a second portion of the X-ray images acquired by the image acquiring means after the contrast media injected by the injection means reaches the region of interest of the subject to obtain X-ray subtraction images;
   second image storing means for storing the X-ray subtraction images obtained by the subtraction means;
   detecting means for generating a memory selection signal upon detecting a selected state of the subject;

selection means for selecting the second image storing means in accordance with the memory detection signal;
superimposition means for superimposing the X-ray subtraction images stored in the second image storing means on third X-ray images acquired by the image acquiring means to obtain X-ray superimposition images; and
display means for displaying the X-ray superimposition images obtained by the superimposition means.

9. A system according to claim 8, wherein the detecting means includes:
monitoring means for monitoring electrocardiogram signals of the subject;
R-wave detecting means for detecting R-waves of the electrocardiogram signals monitored by the monitor means; and
means for generating the memory selection signal in accordance with the R-waves detected by the R-wave detecting means.

* * * * *